(12) United States Patent
Arnaud-Sebillotte et al.

(10) Patent No.: US 6,946,124 B2
(45) Date of Patent: Sep. 20, 2005

(54) IRIDESCENT COSMETIC COMPOSITION AND USE THEREOF

(75) Inventors: Laurence Arnaud-Sebillotte, L'Hay-les-Roses (FR); Veronique Guillou, Antony (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/182,704

(22) PCT Filed: Jan. 14, 2002

(86) PCT No.: PCT/FR02/00128
§ 371 (c)(1),
(2), (4) Date: Aug. 7, 2002

(87) PCT Pub. No.: WO02/056854
PCT Pub. Date: Jul. 25, 2002

(65) Prior Publication Data
US 2003/0012802 A1 Jan. 16, 2003

(30) Foreign Application Priority Data
Jan. 18, 2001 (FR) ............................................. 01 00682

(51) Int. Cl.⁷ ................................................ A61K 7/48
(52) U.S. Cl. ..................................... 424/78.02; 424/401
(58) Field of Search ............................. 424/78.02, 401, 424/63, 64

(56) References Cited

U.S. PATENT DOCUMENTS 5,945,095 A * 8/1999 Mougin et al. .......... 424/78.02
5,961,994 A * 10/1999 Cauwet et al. ............... 424/401
2002/0022009 A1 * 2/2002 de la Poterie et al. ........ 424/63

FOREIGN PATENT DOCUMENTS

EP 0 978 271 2/2000
WO 00 47167 8/2000

OTHER PUBLICATIONS

Pan et al.: "Synthesis of highly fluorinated monodisperse colloids for low refractive index crystalline colloidal arrays" Journal of the American Chemical Society, vol. 120, No. 26, pp. 6518–6524, 1998.

* cited by examiner

Primary Examiner—Jyothsna Venkat
(74) Attorney, Agent, or Firm—Oblon, Spivak, McClelland, Maier & Neustadt, P.C.

(57) ABSTRACT

The subject of the present invention is an iridescent composition for topical application, comprising at least one water-soluble surfactant and an aqueous dispersion of particles of polymer, the said particles having a mean size in numerical terms ranging from about 50 to 300 nm. The quantity of particles of polymer being at least 3% by weight of active material relative to the total weight of the composition.

The composition according to the invention has a very attractive visual appearance by virtue of its iridescent color.

The invention also relates to the uses of the composition of the invention in the cosmetic field, in particularly for the treatment, protection, care, removal of make-up from and/or cleansing of the skin, the lips and/or the hair, and/or for the application of make-up to the skin and/or the lips.

17 Claims, No Drawings

IRIDESCENT COSMETIC COMPOSITION AND USE THEREOF

The subject of the invention is an iridescent composition for topical application, comprising at least one water-soluble surfactant and an aqueous dispersion of particles of polymer, the said particles having a mean size in numerical terms ranging from about 50 to 300 nm, and the uses of the said composition, in particular for the treatment, protection, care, removal of make-up from and/or cleansing of the skin, the lips and/or the hair, and/or as make-up for the skin and/or the lips.

Care and/or cleansing compositions for the skin are generally in the form of transparent or white products depending on their constituent ingredients. To make them more attractive, it is possible to colour them by adding various colouring agents thereto. These colouring agents may be, for example, pigments such as lacquers, inorganic pigments or pearlescent pigments, or soluble colorants. However, the colours obtained are often unstable to light.

To obtain iridescent coloured effects, it is possible to use pearlescent pigments with a variety of colours. However, most often, the iridescent effect obtained with these pearlescent pigments is fairly weak, and, in addition, these pigments are difficult to disperse and to maintain in suspension, in particular in cleansing compositions which are often quite fluid. The incorporation of such pigments is therefore delicate and the reproducibility of the effect obtained is not certain.

It has therefore been sought to design products having an iridescent effect without incorporating pearlescent pigments.

The Applicant has found, surprisingly, that the combination of polymers, in the form of particles in dispersion (in emulsion or in latex form), with surfactants, in particular anionic or nonionic surfactants, allows the production of products with an iridescent appearance, which are very attractive for consumers without having the technical difficulties of suspension of the particles.

Indeed, compositions containing a colouring system, which is obtained from colloidal crystalline networks in the medium, giving an iridescent colour without the addition of pigments or colorants, are known from the document WO-00/47167. However, to obtain such an effect, the medium has to have a relatively low ionic strength and a conductance (the conductance is the product of the conductivity of the composition times the measuring cell constant) of less than 2.5 $\mu\Omega^{-1}$, which limits the addition of ionic additives such as ionic surfactants and certain active agents. However, in cosmetic compositions and in particular in cleansing compositions, it is often necessary to introduce ionic compounds into the medium. In addition, it may be advantageous to introduce surfactants into a composition, for example, to solubilize therein perfumes and active agents, or as agents for removing make-up from the skin.

The need therefore remains for an iridescent composition which can retain this iridescent character regardless of the conductance and the ionic strength of its constituent medium.

The Applicant has found, surprisingly, that the disadvantages of the prior art could be remedied using at least 3% by weight of active material of an aqueous dispersion of monodisperse particles of polymer, having a mean particle size in numerical terms ranging from about 50 to 300 nm, and combining water-soluble surfactants therewith.

Accordingly, the subject of the present invention is an iridescent composition for topical application comprising at least one water-soluble surfactant and monodisperse particles of polymer in aqueous dispersion, the said particles having a mean size in numerical terms ranging from 50 to 300 nm and the quantity of the said particles being at least 3% by weight of active material relative to the total weight of the composition.

"Mean size in numerical terms" refers to the mean diameter in numerical terms of the preferably spherical particles of polymer of the dispersion, this size being the original size of the particles before they are mixed with other constituents. Indeed, the size of the particles may be different before and after their incorporation into a composition, because, as described below, the particles may consist of polymer comprising a monomer which is soluble or which swells in alkaline media, such that the particles of polymer may swell in water or alkaline media after incorporation into the composition for topical application.

The size of the particles is measured by means of the Brookhaven 90Plus particle size analyser. The measurements are carried out at 90°.

Moreover, the quantity of particles in the present application is indicated by weight of active material, that is to say by weight of dry matter content of particles of polymers.

The composition of the invention is characterized by its iridescent effect and it has the advantage of having this iridescent effect, regardless of the value of its conductance (expressed in ohm$^{-1}$ or in Siemens).

Macroscopically, the iridescent effect results in variations in colour which are perceived by an observer who would be moving around the surface of the product illuminated by a fixed light beam. By contrast, a product is not iridescent when the observer does not see a change in colour during their movement.

The iridescent effect may be measured by means of a goniometer, the principle of which is to measure the colour by varying the geometric conditions of observations (angles of illumination and of detection of the reflected light). The method of measurement used here and described in greater detail below is inspired by that described in "Color effects from thin film designs" by Roger Phillips, Mike Nofi and Robert Slusser (Flex Products Inc 2793 Nothpoint Parkway Santa Rosa Calif. 95407).

Method of Measurement:

The samples, at the temperature of 23° C., fill a vessel 5 mm in height. Their top surface is placed in the plane of measurement of a spectrophotogoniometer. The spectra are measured as a reflexion at 400–760 nm in steps of 5 nm. The spectra are recorded at an angle of illumination set at 55° and at angles of detection placed successively at the following values: 90° (scattering), 100, 110, 120, 130 and 140°. This path simulates the variations perceived by an observer who would be moving around the surface of the product illuminated by a fixed light beam.

The different spectra thus obtained are processed in order to obtain the calorimetric parameters L*a*b* in the CIELAB space (reference: ceramic bore MINOLTA Number 20231050 at the illumination D65 Y=94.1, x=0.3157, y=0.3331). The colour path is obtained by joining in the plane of abscissa a* and of ordinate b*, the coordinates of the colorimetric values calculated. a* varies from green to red and b* varies from blue to yellow. When a* is negative, the colour possesses a dominant green; when it is positive, the colour possesses a dominant red. When b* is negative, the colour possesses a dominant blue; when it is positive, the colour possesses a dominant yellow. The calorimetric difference is equal to the square root of the sum of the squares of the differences in the values a and b relative to the first measurement (detection angle of 90 degrees, a measurement close to that obtained with a conventional colorimeter such as the chromameter MINOLTA CR300).

Thus, a composition has an iridescent appearance when the colorimetric difference for this composition or for the dispersion of particles of polymer which it contains is greater than 2, and preferably varies from 2 to 100, preferably from 3 to 60 for an angle of illumination of 55° and an angle of detection of between 100 and 140° as described above. The incident light is characterized by a beam having a diameter of 8 mm, an angular resolution of 1.3 degrees, a wavelength of 250 to 800 nm and a 1 nm type resolution.

A product which does not possess an iridescent effect is characterized, for example, by differences varying from 0.1 to 1 under the same measurement conditions.

The composition of the invention is also characterized by its turbidity, that is to say its opacity. The turbidity measures the opacity of a product. The NTU (Nephelometric Turbidity Units) are the units of measurement of the turbidity of a composition. The measurement of turbidity may be carried out, for example, with a turbidimeter model 2100P from the company HACH, the tubes used for the measurement being identified by the references AR397A cat 24347-06. The measurements are carried out at room temperature (20° C. to 25° C.). The higher the turbidity, the greater the opacity of the product. The composition of the invention is generally translucent to opaque and it preferably has a turbidity greater than 100.

Moreover, the composition according to the invention generally has a viscosity ranging from 0.1 poise to 100 poises (0.01 Pa.s to 10 Pa.s), preferably from 4 to 70 poises (0.4 to 7 Pa.s) and more preferably from 5 to 30 poises (0.5 to 3 Pa.s), this viscosity being measured at about 25° C. with a Rheomat 180 apparatus using a 2, 3, 4 or 5 rotor depending on the viscosity range, at 200 s$^{-1}$.

The composition of the invention is a composition for topical, and in particular cosmetic, use, and, as such, it contains a physiologically acceptable medium, that is to say a medium compatible with the skin, the hair, the nails and/or the mucous membranes (lips). In addition, it preferably has a pH compatible with the skin, that is to say preferably ranging from 3 to 8 and, even better, from 5 to 7. This pH value may depend on the type of polymer used.

The polymer particles used in the composition of the invention should be monodisperse, that is to say that the results of measurements of the diameter of the particles are statistically distributed around a mean and according to a single Gaussian curve. The variation relative to the mean should not exceed 10% per 100% of particles. This means that the particles practically all have the same size. This size ranges from 50 to 300 nm, preferably from 90 to 230 nm and even better from 100 to 200 nm. The size of the particles is measured by means of the Brookhaven 90Plus particle size analyser. The measurements are carried out at 90°.

The particles consist of polymers. They become suspended or dispersed in water, in latex or emulsion form. Latexes are aqueous dispersions of particles of polymers, as described in "An introduction to polymer colloids" by F. CANDAU and R. H. OTTEWILL, Kluwer Academic Publishers, March 1989. The term polymer is understood here to mean both homopolymers obtained from a single type of monomer and copolymers obtained from several types (two or more) of monomers. These polymers may be either associative polymers (that is to say possessing a hydrophobic part and a hydrophilic part) or nonassociative polymers (that is to say hydrophilic or water-soluble). They are dispersible in water and may exhibit swelling in alkaline media (or alkaline-swelling) or not. The polymers may be of any type: nonionic, anionic, cationic, zwitterionic or ampho-teric.

The particles which can be used in the composition of the invention preferably consist of ionic polymers and even better anionic polymers. These polymers are dispersible in water and preferably exhibit alkaline-swelling. The preferred polymers possess at least one monomer soluble in alkaline media, such as monomers of acrylic, methacrylic, vinylacetic, maleic, crotonic and itaconic acids. They may contain another monomer such as styrene, butadiene, ethylene, acrylonitrile, chloroprene, vinylidene chloride, isoprene, isobutylene, vinyl chloride, and esters of acrylic, methacrylic, vinylacetic, maleic, crotonic and itaconic acids and mixtures thereof.

Thus, the polymer particles may be chosen, for example, from the particles consisting of the following anionic polymers:

1) homopolymers of acrylic acid, such as those of the dispersions (in aqueous emulsion) marketed under the names MIRACARE XC 96/36, MIRACARE XC 96/37 and MIRACARE XC 96/52 (acrylic nanolatex) by the company RHODIA CHIMIE.

2) copolymers of acrylic acid and of other monomers, such as those of the dispersions marketed under the names NEOCRYL PD-723-B (particle size: 114 nm), NEOCRYL XK 90 (particle size: 109 nm), NEOCRYL XK 53 (particle size: 96 nm) by the company AVECIA RESINS; ECOCRYL VS 301 (particle size: 150 nm) by the company ATOCHEM; NEOCRYL XK-75 (particle size: 102 nm) (aqueous emulsion of an acrylic acid/butyl methacrylate/methyl methacrylate/butyl acrylate copolymer) by the company AVECIA RESINS; MIRACARE XC 97-8 to 13 (acrylic/methyl methacrylate/butyl acrylate/methacrylic acid copolymer and derivatives in nonionic aqueous nanoemulsion) by the company RHODIA CHIMIE, ACRYSOL 33 (or ACULYN 33) (acrylic acid/ethyl acrylate copolymer) (particle size: 110 nm) by the company ROHM & HMS.

3) styrene derivatives, such as those of the dispersions marketed under the name SETALUX 6801 AQ 24 (styrene/butyl acrylate/methyl methacrylate/methacrylic acid hybrid copolymer) (particle size: 186 nm) by the company AKZO NOBEL; under the name RHODOPAS GS 125 (particle size: 170 nm) by the company RHONE POULENC, under the names NEOCRYL XK 61 (anionic acrylic/styrene copolymer) (particle size: 76 nm), NEOCRYL A 1079 (styrene/acrylate copolymer) (particle size: 115 nm) by the company AVECIA RESINS; under the name RK-3-59A-PMN (mixture of two styrene/acrylic polymers (nucleus/envelope)) (particle size: 116 nm) by the company ROHM-HAAS, under the name DOW LATEX 432 (styrene/acrylate copolymer) (particle size: 145 nm) by the company LAMBERT-RIVIERE, under the name SCX 8060 (particle size: 116 nm) by the company JOHNSON POLYMER France.

4) fluorinated derivatives, such as those of the dispersions marketed under the references LUMIFLON E-3029 (anionic aqueous dispersion containing 50% of hydroxylated fluorinated polymer) (particle size: 100 nm) and LUMIFLON FE-3000 (anionic aqueous dispersion containing 50% of hydroxylated fluorinated polymer (particle size: 150 nm) by the company ASAHI GLASS.

5) silicone-based derivatives, such as that of the dispersion marketed under the reference HYCAR 26348 (acrylates/acrylonitrogen/siloxane copolymer) (particle size: 133 nm) by the company GOODRICH.

6) diisocyanate derivatives, such as that of the dispersion marketed under the reference NEOPAC E-106 (urethane/acrylate copolymer (and) methylpyrrolidone (and) triethylamine) (particle size: 98 nm) by the company AVECIA RESINS.

According to a preferred embodiment of the invention, particles of acrylic acid/ethyl acrylate copolymer, particles of styrene/butyl acrylate/methyl methacrylate/methacrylic acid hybrid copolymer, that is to say the dispersions sold under the names ACRYSOL 33 or ACULYN 33 by the company ROHM & HAAS and SETALUX 6801 AQ 24 by the company AKZO NOBEL, and mixtures thereof are used. These dispersions are characterized by their colorimetric difference. When the polymer dispersion "ACULYN 33" is used, it is preferable that the composition has a pH value ranging from 3 to 6.3.

| Raw material | Appearance of the raw material | Maximum colorimetric difference | Size of the particles |
|---|---|---|---|
| ACULYN 33 | Iridescent white milk | 12.5 | 110.2 ± 2.4% |
| SETALUX 6801 AQ 24 | Iridescent white milk | 11.1 | 167.7 ± 1.8% |
| Comparative example: SYNTHALEN W2000 ® of 3V SA | Non-iridescent white milk | Less than 1 | 252.2 ± 13.5% with two populations of sizes, one centered around 167 nm and the other around 370 nm |

As shown in the table above, the particles of SYNTHALEN W2000 are not monodisperse, that is to say that their size is not homogeneous and comprises several Gaussian curves. The comparative results presented later show that this polymer dispersion is not appropriate for obtaining an iridescent effect, whereas the two dispersions "ACULYN 33" and "SETALUX 6801 AQ 24" which are monodisperse allow iridescent compositions to be obtained.

The quantity of particles of polymer in the composition of the invention depends on the polymer used. It may range, for example, from 3 to 50%, preferably from 3.5 to 40% and even better from 4 to 30% by weight (of active material or dry matter) relative to the total weight of the composition.

The composition according to the invention contains at least one water-soluble surfactant. The surfactant used may be chosen from nonionic, anionic, zwitterionic and amphoteric water-soluble surfactants and mixtures thereof. The expression "water-soluble surfactant" is understood to mean any surfactant soluble in water at room temperature (about 25° C.). Such surfactants generally have an HLB (Hydrophilic Lipophilic Balance) value equal to or greater than 11.

The total quantity of surfactant(s) may range, for example, by weight of active material, from 0.5 to 50% by weight, preferably from 2 to 40% by weight and even better from 3 to 30% by weight relative to the total weight of the composition.

As surfactants which can be used in the composition of the invention, there may be mentioned for example:

i) Nonionic Surfactants

There may be used as nonionic surfactants, esters of polyols and of fatty acids, esters of polyethylene glycols and of fatty acid, derivatives of fatty alcohols and of polyols (ethers), and oxyalkylenated (oxyethylenated and/or oxypropylenated) derivatives of these compounds.

ii) Anionic Surfactants

There may be used, for example, as anionic surfactants, carboxylates (sodium 2-(2-hydroxyalkyloxy)acetate), derivatives of amino acids (N-acylglutamates, N-acylglycinates, acylsarcosinates), alkyl sulphates, alkyl ether sulphates and their oxyethylenated derivatives, sulphonates, isethionates, N-acylisethionates, taurates and N-acyl-N-methyltaurates, sulphosuccinates, alkyl sulphoacetates, phosphates and alkyl phosphates, polypeptides, anionic derivatives of alkyl polyglycoside (acyl-D-galactoside uronate), soaps of fatty acids, and mixtures thereof.

iii) Amphoteric and Zwitterionic Surfactants

There may be used, for example, as amphoteric and zwitterionic surfactants, betaines, N-alkylamidobetaines and their derivatives, glycine derivatives, sultaines, alkyl polyaminocarboxylates, alkyl amphoacetates, and mixtures thereof.

It is also possible to use a mixture of two or more of these surfactants.

It is possible to choose in particular the surfactant from those indicated in the following list which is not exhaustive:

| Surfactants (CTFA names and tradenames) | HLB |
|---|---|
| Ethoxylated triglyceride (CIRRASOL ALN-WY) | 11 |
| Glycerol monostearate (RHEODOL SEM) | 11 |
| Glyceryl stearate (AND) PEG-100 stearate (ICI) (ARLACEL 165) | 11 |
| PEG alkyl ether (NOIGEN ET 115) | 11 |
| POE glyceryl cocoate (GLYCEROX HE) | 11 |
| POE sorbitan trioleate (RHEODOL TW-0320) | 11 |
| POE-10 monostearate (NIKKOL MYS-10) | 11 |
| POE-20 POP-6 decyltetradecylether (NIKKOL PEN-4620) | 11 |
| POE-20 sorbitan trioleate (ALKAMULS PSTO-20) | 11 |
| POE-20 sorbitan trioleate (MONTANOX 85) | 11 |
| POE-20 sorbitan trioleate (NIKKOL TO-30) | 11 |
| POE-20 sorbitan trioleate (POLYSORBATE 85) (TO-55-F) | 11 |
| POE-20 sorbitan trioleate (RHEODOL SUPER TW-0320) | 11 |
| POE-20 sorbitan trioleate (TWEEN 85) | 11 |
| POE-30 hydrogenated castor oil (NIKKOL HCO-30) | 11 |
| POE-30 sorbitan tristearate (NIKKOL TS-30) | 11 |
| POE-8 glyceryl monolaurate (GLYCEROX L8) | 11 |
| Saccharose mono/distearate (SUCRO ESTER WE 11) | 11 |
| PEG-8 stearate (ICI) (MYRJ 45) | 11.1 |
| POE-8 stearate (SIMULSOL M 45) | 11.1 |
| POE sorbitol oleate (SORBON TR 843) | 11.2 |
| (EUMULGIN C8) | 11.4 |
| Alkylaryl sulphonate (ATLAS G 3300B) | 11.4 |
| POE sorbitol hexaoleate (ATLAS G-1096) | 11.4 |
| POE sorbitol oleate laurate (ATLOX 1045 A) | 11.4 |
| POE-6 tridecyl alcohol (RENEX 36) | 11.4 |
| Di-POE-8 alkyl ether phosphate (NIKKOL DDP-8) | 11.5 |
| Ethoxylated alcohol (BEROL 087) | 11.5 |
| PEG monooleate (ABLUNOL 400 MO) | 11.5 |
| PEG monooleate (NISSAN NONION 0-4) | 11.5 |
| PEG-400 monooleate (PGE-400-MO) | 11.5 |
| PEG-400 monostearate (PGE-400 MS) | 11.5 |
| POE-30 sorbitol tetraoleate (NIKKOL GO-430) | 11.5 |
| POE-7 cetyl ether (NIKKOL BC-7) | 11.5 |
| Sorbitol POE-55 hexaoleate (SORBETH 55HO) | 11.5 |
| Tri-POE-8 alkyl ether phosphate (NIKKOL TDP-8) | 11.5 |
| PEG monostearate (ABLUNOL 400 MS) | 11.6 |
| PEG-400 monooleate (RADIASURF 7403) | 11.7 |
| (SYNPERONIC 91/5) | 11.8 |
| OE castor oil (ABLUNOL CO 30) | 11.8 |
| POE monooleate (IONET MO-400) | 11.8 |
| POE polyol fatty acid esters (RHEODOL 440) | 11.8 |
| Coceth-7 (NIOX KG-83) | 11.9 |
| PEG-400 stearate (RADIASURF 7413) | 11.9 |
| POE cetyl ether (NISSAN NONION P-208) | 11.9 |
| (SYNPERONIC 87K) | 12 |
| (SYNPERONIC BD100) | 12 |
| Citric ester of monoglycerides(IMWITOR 369) | 12 |
| Decaglycerin monolinoleate (NIKKOL DECAGLYN 1-LN) | 12 |
| Decagycerin distearate (NIKKOL DECAGLYN 2-S) | 12 |
| Ethylene glycol mono/distearate (TEGIN G) | 12 |
| Glycerol mono/distearate (TEGIN 4433) | 12 |
| Glycerol mono/distearate (TEGIN SPECIAL) | 12 |
| Glycerol mono/distearate (TEGIN) | 12 |
| Glycerol mono/distearate + autres nonioniques (TEGINACID) | 12 |
| Glyceryl mono/distearate et fatty alcohol sulfates (TEGINACID SPECIAL) | 12 |
| PEG alkyl ether (NOIGEN ET 127) | 12 |
| PEG oleic acid ester (NOIGEN ES 120) | 12 |
| PEG oleyl ether (NOIGEN ET 120) | 12 |
| PEG-400 monolaurate (PGE-400-ML) | 12 |
| PG mono/distearate (TEGIN P) | 12 |
| POE-30 POP-6 decyltetradecylether (NIKKOL PEN-4630) | 12 |
| Polysorbate 21/POE-4 sorbitan monolaurate (ML-55-F-4) | 12 |
| Fatty alcohol polyglycol ether (AKYPOROX RO 90) | 12.1 |
| POE alkyl ether (ABLUNOL LA 7) | 12.1 |
| POE lauryl ether (NISSAN NONION K-207) | 12.1 |
| OE castor oil (EMULPON EL 33) | 12.2 |
| Pareth-45-8 (NIOX KQ-81) | 12.2 |
| POE alkylaryl ether (EMULGEN 910) | 12.2 |
| Alkylaryl PG ether (MARLOWET ISM) | 12.3 |

| Surfactants (CTFA names and tradenames) | HLB |
|---|---|
| C12–C14 alcohol polyglycol ether (MARLIPAL 14/70) | 12.3 |
| PG-600 oleate (ETHYLAN A6) | 12.3 |
| PEG-10 tallow amine (ETILENOX LM-11) | 12.4 |
| POE-10 oleyl alcohol (BRIJ 96) | 12.4 |
| POE-10 oleyl alcohol (SIMULSOL 96) | 12.4 |
| POE-10 stearyl alcohol (BRIJ 76) | 12.4 |
| POE-10 stearyl alcohol (SIMULSOL 76) | 12.4 |
| POE-35 hydrogenated castor oil (CRODURET 35) | 12.4 |
| (SYNPERONIC A9) | |
| Alkylaryl polyether alcohol (TRITON X-155-90%) | 12.5 |
| Decaglycerin monoisostearate (NIKKOL DECAGLYN 1-IS) | 12.5 |
| Decaglycerin monostearate (NIKKOL DECAGLYN 1-S) | 12.5 |
| Fatty alcohol polyglycol ether carboxylic acid (AKYPO LF 1) | 12.5 |
| Oleth-10 (NOIOX KJ-32) | 12.5 |
| POE alkyl aryl ether (NISSAN DISPANOL N-100) | 12.5 |
| POE sorbitan esters of mixed fatty and resin acids | 12.5 |
| (ATLAS G-8936CJ) | |
| POE-10 phytosterol (NIKKOL BPS-10) | 12.5 |
| POE-40 castor oil (NIKKOL CO-40TX) | 12.5 |
| POE-40 hydrogenated castor oil (NIKKOL HCO-40) | 12.5 |
| POE-40 sorbitol tetraoleate (NIKKOL GO-440) | 12.5 |
| POE-5,5 alkyl alcohol (SYNTHENS KMA 55) | 12.5 |
| POE-POP cethyl ether (NIKKOL BPC-44) | 12.5 |
| C16–C18 alcohol polyglycol ether (MARLIPAL 1618/10) | 12.6 |
| Coceth-8 (NIOX KG-82) | 12,6 |
| OE fatty alcohol (BEROL 065) | 12.6 |
| Oleyl/cetyl alcohol polyglycol ether (EUMULGIN ET 10) | 12.6 |
| OE isotridecanol (NIOX KP-69) | 12,7 |
| C13-oxoalcohol polyglycol ether (MARLIPAL 013/80) | 12.8 |
| OE branched fatty alcohol (LAUROPAL X 1107) | 12.8 |
| OE fatty oxoalcohol (NIOX KQ-55) | 12.8 |
| OE saturated linear fatty alcohol (NIOX KL-16) | 12.8 |
| PEG monostearate (NISSAN NONION S-15) | 12.8 |
| POE laurate (ATLAS G-2127) | 12.8 |
| POE lauryl alcohol (ATLAS G-3707) | 12.8 |
| (ARQUAD T-2C-50) | 12.9 |
| Alkyl polyethoxyether (NIOX BD-63) | 12.9 |
| C12–C14 alcohol polyglycol ether (MARLIPAL 24/80) | 12.9 |
| POE dioleate (IONET DO-1000) | 12.9 |
| POE-10 cetyl alcohol (BRIJ 56) | 12.9 |
| POE-40 hydrogenated castor oil (CRODURET 40) | 12.9 |
| Polyoxyetylene cetyl ether (NISSAN NONION P-210) | 12.9 |
| Alkyl aryl ethoxylated (ETHYLAN BKL 130) | 13 |
| Citric ester of monoglyceride (IMWITOR 370) | 13 |
| Fatty alcohol polyglycol ether (MULSIFAN RT 19) | 13 |
| Hexaglycerin monolaurate ( NIKKOL HEXAGLYN 1-L) | 13 |
| OE fatty alcohol (LAUROPAL 0207L) | 13 |
| OE fatty oxoalcohol (NIOX KQ-20) | 13 |
| OE technical castor oil (EUMULGIN RT 40) | 13 |
| PEG alkyl ether (NOIGEN ET 135) | 13 |
| PG laurate (CHIMIPAL APG 400) | 13 |
| POE-60 sorbitol tetrastearate (NIKKOL GS-460) | 13 |
| Sucrose fatty acid ester (DK ESTER F 140) | 13 |
| C16–C18 alcohol polyglycol monolaurate | 13.1 |
| (NISSAN NONION L-4) | |
| PEG monolaurate (ABLUNGL 400 ML) | 13.1 |
| POE alkylaryl ether (EMULGEN 810) | 13.1 |
| POE lauryl ether (PEGNOL L-8) | 13.1 |
| Anionic and nonionic surfactant (ATLOX 4851 B) | 13.2 |
| OE fatty alcohol (LAUROPAL 9) | 13.2 |
| PEG-400 monolaurate (RADIASURF 7423) | 13.2 |
| PEG-600 monooleate (RADIASURE 7404) | 13.2 |
| PEG-600 monostearate (RADIASURF 7414) | 13.2 |
| POE lauryl ether (NISSAN NONION DN-209) | 13.2 |
| C13-oxoalcohol polyglycol ethers (MARLIPAL 13/90) | 13.3 |
| PEG-4 sorbitan monolaurate (ICI) (TWEEN 21) | 13.3 |
| POE alkyl ether (ABLUNOL LA 9) | 13.3 |
| POE laurate (ATLAS G2109) | 13.3 |
| POE sorbitan monolaurate (RHEODOL TW-L106) | 13.3 |
| POE-5 sorbitan monolaurate (MONTANOX 21) | 13.3 |
| C12–C14 alcohol polyglycol ether (MARLIPAL 14/90) | 13.4 |
| Cetareth-12 (NIOX KJ-71) | 13.4 |
| Fatty alcohol polyglycol ether (DEHYDOL TA 12) | 13.4 |
| Nonionic and anionic (ABLUMUL AG-AH) | 13.4 |
| POE mono coco-fatty acid ester (VALUE 1209C) | 13.4 |
| Decaglicerin monooleate (NIKKOL DECAGLYN 1-O) | 13.5 |
| Di-POE-10 alkyl ether phosphate (NIKKGL DDP-10) | 13.5 |
| OE amide (ETHOMID HT/15) | 13.5 |
| OE castor oil (EMULPON EL 40) | 13.5 |
| OE fatty alcohol (BEROL 048) | 13.5 |
| OE fatty alcohol (BEROL 185) | 13.5 |
| PEG glycol monooleate (ABLUNGL 600 MO) | 13.5 |
| PEG monooleate (NISSAN NONION O-6) | 13.5 |
| PEG-600 monooleate (PGE-600-MO) | 13.5 |
| PEG-600 monostearate (PGE-600-MS) | 13.5 |
| POE-50 hydroxygenated castor oil (NIKKOL HOG-50) | 13.5 |
| PGE-cethyl ether (NIKKOL BC-10TX) | 13.5 |
| Quaternary ammonium (ARQUAT S-2C-50) | 13.5 |
| Amino acid (ARMEEN SZ) | 13.6 |
| Amino acid (ARMEEN Z) | 13.6 |
| OE castor oil (ABLUNOL CO 45) | 13.6 |
| OE fatty acid (CIRRASOL ALN-TF) | 13.6 |
| OE fatty acid (CIRRASOL ALN-TS) | 13.6 |
| PEG monostearate (ABLUNOL 600 MS) | 13.6 |
| PEG monostearate (NISSAN NONION S-6) | 13.6 |
| POE alkyl ether (ATLOX 4991) | 13.6 |
| POE alkyl ether (ATLOX 4995) | 13.6 |
| POE fatty alcohol ether (EMULGEN 420) | 13.6 |
| POE monooleate (VALUE 1414) | 13.6 |
| C13-oxoalcohol polyglycol ether (MARLIPAL 013/100) | 13.7 |
| Nonionic (ATLOX 5325) | 13.7 |
| C12 alcohol polyglycol ether (MALIPAL 129) | 13.8 |
| PEG palmitate (NISSAN NONION P-6) | 13.8 |
| POE polyol fatty acid esters (RHEODOL 450) | 13.8 |
| C12–C14 alcohol polyglycol ether (MARLIPAL 14/100) | 13.9 |
| Nonionic and anionic (ABLUMUL AG-KP3) | 13.9 |
| OE cetostearyl alcohol (ATLAS G-4822) | 13.9 |
| POE fatty alcohol polyglycol ether (EMULGEN 320 P) | 13.9 |
| POE-11 C13–C15 alcohol (RENEX 711) | 13.9. |
| Alkyl aryl polyether (TRITON CF-10) | 14 |
| Fatty alcohol ether sulfosuccinate (REWOPOL SB FA 50) | 14 |
| OE amides (ETHOMID O/15) | 14 |
| PEG lauryl ether (NOIGEN ET 147) | 14 |
| PEG oleic acid ester (NOIGEN ES 140) | 14 |
| PEG oleyl ether (NOIGEN ET 140) | 14 |
| POE alkyl ether (ATLOX 804) | 14 |
| POE-15 glyceryl monolaurate (GLYCEROX L 15) | 14 |
| PGE-24 cholesterol (SOLULAN C-24) | 14 |
| PGE-60 castor oil (NIKKOL CO-60TX) | 14 |
| POE-60 sorbitol tetraoleate (NIKKOL GO-460) | 14 |
| Saccharose monopalmitate (SUCRO ESTER WE 15) | 14 |
| Cetareth-14 (NIOX KJ-61) | 14.1 |
| POE cetyl ether (NISSAN NONION P-213) | 14.1 |
| POE lauryl ether (NISSAN NONION K-211) | 14.1 |
| C12-C14 alcohol polyglycol ether (MARLIPAL 24/110) | 14.2 |
| Fatty alcohol polyglycol ether carboxylic acid (AKYPO LF 6) | 14.2 |
| OE alcohol (QUIMIPOL EA 2512) | 14.2 |
| POE fatty alcohol ether (Emulgen 220) | 14.2 |
| POE oleyl ether (NISSAN NONION E-215) | 14.2 |
| POE stearyl ether (NISSAN NONION S-215) | 14.2 |
| Quaternary ammonium (ARQUAD T-50) | 14.2 |
| Free acid of complex organic phosphate ester | 14.4 |
| (PLYSURF A216B) | |
| OE fatty alcohol (LAUROPAL 11) | 14.4 |
| OE fatty alcohol (LAUROPAL 1150) | 14.4 |
| PEG-12 cocamine (ETILENOX KM-54) | 14.4 |
| POE alkyl ether (ABLUNOL LA 12) | 14.4 |
| POE castor oil (ARLATONE 285) | 14.4 |
| POE cetyl ethr (PEGNOL C-14) | 14.4 |
| POE hydrogenated castor oil (ARLATONE 289) | 14.4 |
| POE triglyceride (ATLAS G-1285) | 14.4 |
| POE triglyceride (ATLAS G-1289) | 14.4 |
| POE triglyceride (ATLOX 1285) | 14.4 |
| C13 oxoalcohol polyglycol ethers (MARLIPAL 013/120) | 14.5 |
| Decaglycerin monomyristate (NIKKOL DECAGLYN 1-M) | 14.5 |
| OE ethylene diamine POP (ALKATRONIC EDP 38-4) | 14.5 |
| POE-10 oleyl ether (NIKKOL BO-10TX) | 14.5 |
| POE-12 tridecyl alcohol (RENEX 30) | 14.5 |
| POE-60 hydrogenated castor oil (NIKKOL HCO-60) | 14.5 |
| POE-9 lauryl ether (NIKKOL BL-9EX) | 14.5 |
| (SYNPERONIC 91/10) | |
| C12–C14 alcohol polyglycol ether (MARLIPAL 24/120) | 14.6 |
| Fatty alcohol ethylene oxide condenste (EMPILAN KA 1080) | 14.6 |
| OE fatty amines (ETHOMEEN S/12) | 14.6 |

-continued

| Surfactants (CTFA names and tradenames) | HLB |
|---|---|
| OE-OP (NEWPOL PE-88) | 14.6 |
| OE fatty oxoalcohol (NIOX KQ-57) | 14.7 |
| POE-60 hydrogenated castor oil (CRODURET 60) | 14.7 |
| (SYNPERONIC 13/12) | 14.8 |
| OE-OP (NEWPOL PE-78) | 14.8 |
| PEG monolaurate (ABLUNOL 600 ML) | 14.8 |
| POE lauryl ether (PEGNOL L-12) | 14.8 |
| (PLYSURF A217E) | 14.9 |
| Fatty alcohol OE (CIRRASOL ALN-WF) | 14.9 |
| OE fatty amines (ETHOMEEN T/12) | 14.9 |
| GE-OP (NEWPOL PE-68) | 14.9 |
| PEG-20 sorbitan monostearate (ICI) (1204) (TVVEEN 60) | 14.9 |
| POE sorbitan monostearate (IONET T-60C) | 14.9 |
| POE sorbitan monostearate (NISSAN NONION ST-221) | 14.9 |
| PGE-16 cetyl alcohol (ATLAS G-3816) | 14.9 |
| POE-20 sorbitan monolaurate (ALKAMULS PSMS-20) | 14.9 |
| POE-20 sorbitan monooleate (RADIAMULS SORB 2157) | 14.9 |
| PGE-20 sorbitan monostearate (EMASOL S-120) | 14.9 |
| POE-20 sorbitan monostearate (MONTANOX 60) | 14.9 |
| POE-20 sorbitan monostearate (NIKKOL TS-10) | 14.9 |
| Ethoxylated polyoxypropylene glycols | 15 |
| (ALKATRONIC PGP 18-4) | |
| OE (PEPOL B-184) | 15 |
| OE fatty alcohol (BEROL 07) | 15 |
| OE sorbitan ester (SORBANOX AOM) | 15 |
| OE sorbitan ester (SORBANOX AST) | 15 |
| GE-20 methyl glucoside sesquistearate | 15 |
| (GLUCAMATE SSE-20) | |
| Oleth-18 (NOIOX KJ-23) | 15 |
| Oleth-20 (AMEROXOL OE-20) | 15 |
| PEG oleyl ether (NOIGEN ET 157) | 15 |
| PEG-20 sorbitan monooleate (ICI) (TWEEN 80) | 15 |
| PEG-20 stearate (ICI) (MYRJ 49) | 15 |
| PEG-600 monolaurate (PGE-600-ML) | 15 |
| POE sorbitan monolaurate (ABLUNOL T 80) | 15 |
| POE sorbitan-20 monooleate (ALKAMULS PSMO-20) | 15 |
| POE-20 sorbitan monoisotearate (NIKKGL TI-10) | 15 |
| POE-20 sorbitan monooleate (ATLAS G-4905) | 15 |
| POE-20 sorbitan monooleate (TWEEN 80) | 15 |
| POE-20 sorbitan monooleate (MONTANOX 80) | 15 |
| POE-20 stearate (MYRJ 49) | 15 |
| POE-20 stearate (SIMULSOL M 49) | 15 |
| POE-25 monostearate (NIKKOL MYS-25) | 15 |
| POE-80 hydrogenated castor oil (NIKKOL HCO-80) | 15 |
| Sucrose fatty acid esters (DK ESTER F 160) | 15 |
| Sucrose monococoate (CRODESTA SL 40) | 15 |
| Tri POE-10 alkyl ether phosphate (NIKKOL TDP-10) | 15 |
| C16–C18 alcohol polyglucol ether (MALIPAL 1618/18) | 15.1 |
| Nonionic and anionic (ABLUMOL AG-420) | 15.2 |
| PEG alkyl ether (ABLUNOL LA 16) | 15.2 |
| PEG monooleate (ABLUNOL 1000 MO) | 15.2 |
| PEG monostearate (ABLUNOL 1000 MS) | 15.2 |
| POE lauryl ether (NISSAN NONION K-215) | 15.2 |
| C13 oxoalcohol polyglycol ethers (MARLIPAL 013/150) | 15.3 |
| Ceteareth-20 (NIOX EO-41) | 15.3 |
| Oleth-20 (ICI) (2101) (BRIJ 98) | 15.3 |
| Oleth-20 (SIMULSOL 98) | 15.3 |
| POE cetyl ether (PEGNOL C-18) | 15.3 |
| POE fatty alcohol ether (EMULGEN 120) | 15.3 |
| POE oleyl ether (NISSAN NONION E-220) | 15.3 |
| POE sorbitan monopalmitate (NISSAN NONION S-220) | 15.3 |
| POE sorbitan monostearate (SORBON T-60) | 15.3 |
| Steareth-20 (BRIJ 78) | 15.3 |
| Steareth-20 (SIMULSOL 78) | 15.3 |
| Fatty alcohol polyglycol ether (DEHYDOL TA-20) | 15.5 |
| PEG-1000 monostearate (PGE-1000-MS) | 15.5 |
| POE sorbitan monolaurate (ABLUNOL T40) | 15.5 |
| POE sorbitan monooleate (RHEODOL TW-O120) | 15.5 |
| POE-15 cetyl ether (NIKKOL BC-15TX) | 15.5 |
| POE-20 ceto/stearyl ether (CETOMACROGOL 1000 BP) | 15.5 |
| POE-20 phytosterol (NIKKOL BPS-20) | 15.5 |
| Quaternary ammonium (ARQUAD S-50) | 15.5 |
| Steareth-21 (ICI) (BRIJ 721) | 15.5 |
| POE lauryl ether (PEGNOL L-15) | 15.6 |
| POE-20 sorbitan monopalmitate (MONTANOX 40) | 15.6 |
| POE-20 sorbitan monopalmitate (TWEEN 40) | 15.6 |
| Ceteth-20 (BRIJ 58) | 15.7 |

-continued

| Surfactants (CTFA names and tradenames) | HLB |
|---|---|
| Isohexadeceth-20 (arlasolve 200) | 15.7 |
| POE cetyl ether (PEGNOL C-20) | 15.7 |
| POE monostearate (IONET MS-1000) | 15.7 |
| POE sorbitan monooleate (RADIASURF 7157) | 15.7 |
| POE sorbitan monopalmitate (SORBON T-40) | 15.7 |
| Quaternary ammonium (ARQUAD 18-50) | 15.7 |
| C13 oxoalcohol polyglycol ether (MARLIPAL 013/170) | 15.8 |
| Quaternary ammonium (ARQUAD 16-50) | 15.8 |
| Noionic (EMULGATOR E2568) | 16 |
| OE-OP ethylene diamine (ALKATRONIC EDP 8-4) | 16 |
| Oleth-15 (NIKKOL BO-15TX) | 16 |
| PEG lauryl ether (NOIGEN ET 160) | 16 |
| PEG oleic acid ester (NOIGEN ES 160) | 16 |
| POE sorbitan monolaurate (RADIASURE 7137) | 16 |
| POE trigyceride (ATLAS G-1288) | 16 |
| POE-20 sorbitan monopalmitate (MP-55-F) | 16 |
| POE-30 stearate (MYRJ 51) | 16 |
| POE-30 stearic acid (SIMULSOL M 51) | 16 |
| (PLYSURF A219B) | 16.2 |
| (SYNPERONIC 13/18) | 16.2 |
| (SYNPERONIC A20) | 16.2 |
| C16-C18 alcohol polyglycol ether (MARLIPAL 1618/25) | 16.2 |
| POE lauryl ether (NISSAN NONION K-220) | 16.2 |
| POE-100 hydrogenated castor oil (CRODURET 100) | 16.3 |
| (SYNPERONIC 13/20) | 16.4 |
| POE-20 sorbitan monolaurate (RADIAMULS SORB 2137) | 16.4 |
| PEG-1500 monostearate (RADIASURF 7417) | 16.5 |
| POE lauryl ether (PEGNOL L-20) | 16.5 |
| POE-100 hydrogenated castor oil (NIKKOL HCO-100) | 16.5 |
| POE-20 behenyl ether (NIKKOL BB-20) | 16.5 |
| POE-POP cetyl ether (NIKKOL PBC-34) | 16.5 |
| Quaternary ammonium (ARQUAD C-33W) | 16.5 |
| POE oleyl ether (NISSAN NONION E-230) | 16.6 |
| Ceteareth-30 (NIOX EO-42) | 16.7 |
| PEG monostearate (NISSAN NONION S-15,4) | 16.7 |
| POE sorbitan monolaurate (ABLUNOL T 20) | 16.7 |
| POE sorbitan monolaurate (IONET T-20C) | 16.7 |
| POe-20 sorbitan monolaurate (EMASOL L-120) | 16.7 |
| POE-20 sorbitan monolaurate (MONTANOX 20) | 16.7 |
| POE-20 sorbitan monolaurate (TWEEN 20) | 16.7 |
| Laureth-23 (BRIJ 35) | 16.9 |
| PEG-40 stearate (ICI) (MYRJ 52) | 16.9 |
| POE-20 sorbitan monolaurate (NIKKOL TL-10) | 16.9 |
| POE-40 stearic acid 5SIMULSOL M 52) | 16.9 |
| PPG PEG (EPAN U 105) | 16.9 |
| Decaglycerin monolaurate (NIKKOL DECAGLYN 1-L) | 17 |
| PEG lauryl ether (NOIGEN ET 170) | 17 |
| POE-20 cetyl ether (NIKKOL BC-20TX) | 17 |
| POE-20 oleyl ether (NIKKOL BO-20) | 17 |
| POE-23 lauryl ether (AMEROXOL LE-23) | 17 |
| POE-40 glyceryl monolaurate (GLYCEROX L 40) | 17 |
| POE-40 stearate (RS-55-40) | 17 |
| C12–C14 alcohol polyglycol ether (MARLIPAL 24/300) | 17.4 |
| POE alkyl amine (PEGNOL OA-400) | 17.4 |
| POE alkylaryl ether (emulgen 935) | 17.5 |
| POE sorbitol oleate (SORBON TR 814) | 17.5 |
| POE triglyceride (ATLAS G1295) | 17.5 |
| Sodium N-decyl diphenyl oxide disulfonate (DOWFAX 3B2) | 17.8 |
| OE fatty amine (ETHMEEN C/15) | 17.9 |
| PEG-50 stearate (ICI) (MYRJ 53) | 17.9 |
| POE-50 stearate (MYRJ 53) | 17.9 |
| OE monodiglyceride of caprylic/capric acids (SOFTIGEN 767) | 18 |
| PEG alkyl ether (NOIGEN ET 187) | 18 |
| PEG oleyl ether (NOIGEN ET 180) | 18 |
| POE-200 castor oil (ETOCAS 200) | 18 |
| POE-200 hydrogenated castor oil (CRODURET 200) | 18 |
| POE-23 cetyl ether (NIKKOL BC-23) | 18 |
| POE-30 behenyl ether (NIKKOL BB-30) | 18 |
| POE-30 phytosterol (NIKKOL NPS-30) | 18 |
| POE-45 monostearate (NIKKOL MYS-45) | 18 |
| POE-50 oleyl ether (NIKKOL BO 50) | 18 |
| POE-55 monostearate (NIKKOL MYS-55) | 18 |
| Sodium lauryl ether sulfate (REWOPOL NL 3-S 70) | 18 |
| PEG monostearate (NISSAN NONION NS-250) | 18.2 |
| POE alkylaryl ether (EMULGEN 950) | 18.2 |
| Amine oxide (AROMOX C/12-W) | 18.4 |
| OE fatty diamine (ETHODUOMEEN T/25) | 18.5 |

-continued

| Surfactants (CTFA names and tradenames) | HLB |
|---|---|
| POE-100 stearate (RS-55-100) | 18.5 |
| POE-25 cetyl ether (NIKKOL BC-25TX) | 18.5 |
| Amine OXIDE (AROMOX DMMCD-W) | 18.7 |
| PEG-100 stearate (ICI) (MYRJ 59) | 18.8 |
| POE-100 stearate (SIMULSOL M 59) | 18.8 |
| Steareth-100 (BRIJ 700) | 18.8 |
| steareth-100 (ICI) (BRIJ 700) | 18.8 |
| POE alkylaryl ether (EMULGEN 985) | 18.9 |
| OE amide (ETHOMIDVHT/60) | 19 |
| OE fatty amine (ETHOMEEN S/15) | 19 |
| PEG distearate (NISSAN NONION DS-6OHN) | 19 |
| PEG fatty acid ester (ABLUNOL 6000 MS) | 19 |
| PEG lauryl ether (NOIGEN ET 190S) | 19 |
| PEG oleyl ether (NOIGEN ET 190S) | 19 |
| POE-21 lauryl ether (NIKKOL BL-21) | 19 |
| OE fatty amine (ETHOMEEN C/25) | 19.3 |
| POE-25 lauryl ether (NIKKOL BL-25) | 19.5 |
| POE-30 cetyl ether (nikkol bc-3Otx) | 19.5 |
| OE fatty amine (ETHOMEEN HT/25) | 19.7 |
| PEG distearate (NOIGEN DS601) | 20 |
| PEG lauryl ether (NOIGEN YX 500) | 20 |
| PEG lauryl ether (NOIGN YX 400) | 20 |
| PEG oleyl ether -NOIGEN O 100) | 20 |
| POE-40 cetyl ether (NIKKOL BC-40TX) | 20 |
| OE POP (ALKATRONIC PGP 40-7) | 22 |
| OE POP (ALKATRONIC PGP 23-7) | 24 |
| PPG PEG (EPAN U 108) | 26 |
| OE POP (ALKATRONIC PGP 33-8) | 27 |
| OE POP ethylene diamine (ALKATRONIC EDP 28-7) | 27 |
| OE POP (ALKATRONIC PGP 23-8) | 28 |
| OE POP (ALKATRONIC PGP 18-8) | 29 |

The physiologically acceptable medium of the composition of the invention comprises water. The quantity of water may range from 30 to 96.5%, preferably from 40 to 95% by weight relative to the total weight of the composition. It may contain, in addition to water, one or more solvents chosen from lower alcohols comprising from 1 to 8 carbon atoms, such as ethanol; polyols such as glycerin; glycols such as butylene glycol, isoprene glycol, propylene glycol, polyethylene glycols such as PEG-8; sorbitol; sugars such as glucose, fructose, maltose, lactose, sucrose; and mixtures thereof. The quantity of solvent(s) in the composition of the invention may range from 0.5 to 30% by weight and preferably from 5 to 20% by weight relative to the total weight of the composition.

The composition of the invention may also contain customary additives in the cosmetic field, such as mattifying inorganic or organic fillers, active agents, preservatives, gelling agents, plasticizers, antioxidants, perfumes, odour absorbers, antifoaming agents, sequestrants (EDTA), acidic or basic pH regulators, or buffers, pigments and pearlescent agents (in a quantity such that this does not disrupt the desired effect), polymers, fatty materials made compatible with the aqueous medium, such as oils or waxes, in so far as the additive does not impair the properties sought for the composition of the invention. The quantities of these various additives are those conventionally used in the fields considered, and for example from 0.01 to 20% of the total weight of the composition.

As active agents, it is possible to incorporate any active agent normally used in the cosmetic and dermatological fields, such as water-soluble or fat-soluble vitamins or provitamins, for example vitamins A (retinol), C (ascorbic acid), B3 or PP (niacinamide), B5 (panthenol), E (tocopherol), K1, beta-carotene, and the derivatives of these vitamins and in particular their esters; hormones or derivatives such as DHEA and 7α-hydroxy DHEA; antiseptics; antiseborrhoeics; antimicrobials such as benzoyl peroxide, salicylic acid, triclosan, azelaic acid, niacinamide (vit. PP); moisturizers such as glycerin, hyaluronic acid, pyrrolidonecarboxylic acid (PCA) and its salts, sodium pidolate, serine, xylitol, trehalose, ectoin, ceramides, urea; keratolytic and antiageing agents such as alpha-hydroxy acids such as glycolic acid, citric acid, lactic acid, beta-hydroxy acids such as salicylic acid, coenzyme Q10; sunscreens; optical brighteners; slimming agents such as caffeine, theophylline, theobromine, anti-inflammatory agents such as 18-β-glycyrrhetinic acid and ursolic acid. It is also possible to use a mixture of two or more of these active agents. The active agent(s) may be, for example, present in a concentration ranging from 0.01 to 20%, preferably from 0.1 to 10% and even better from 0.5 to 5% of the total weight of the composition.

The composition of the invention may be provided in any of the galenic forms normally used in the cosmetic and dermatological fields. It is generally provided in the form of a gel and is prepared according to the customary methods, that is to say by mixing the surfactant and the polymer in the aqueous medium and adjusting the pH if necessary.

The composition according to the invention may comprise an oily phase (or fatty phase) comprising at least one oil, provided that it is solubilized in the medium, for example by forming a microemulsion. The oil(s) may be chosen from oils of plant origin (jojoba, avocado, sesame, sunflower, maize, soyabean, safflower, grapeseed), mineral oils (petroleum jelly, hydrogenated or nonhydrogenated isoparaffins, isohexadecane, squalane), synthetic oils (parleam, isopropyl myristate, cetearyl octanoate, polyisobutylene, ethylhexyl palmitate, alkyl benzoates), volatile or nonvolatile silicone oils such as polydimethylsiloxanes (PDMS) and cyclodimethylsiloxanes or cyclomethicones, and fluorinated or fluorosilicone oils, as well as mixtures of these oils. The oily phase may contain, in addition, other fatty constituents such as fatty alcohols such as stearyl alcohol, cetyl alcohol and the mixture thereof (cetearyl alcohol); fatty acids; waxes; silicone gums. The oily phase may be present in a quantity ranging, for example, from 0.01 to 20% by weight relative to the total weight of the composition.

The composition according to the invention finds application in a large number of treatments, in particular cosmetic treatments, of the skin, including the scalp, the hair, the nails and/or the mucous membranes, in particular for the care, cleansing and/or application of make-up to and/or protection, from the sun, of the skin, the hair and/or the lips or the mucous membranes. It may be used, for example, as products for cleansing or removing make-up from the face (including the eyes and the lips) or the body, as care products for the face, for example for treating the signs of ageing or for moisturizing or nourishing the skin, as antisun products for protecting the skin or the hair from UV radiation, as hair products.

Accordingly, the subject of the present invention is the cosmetic use of the composition as defined above, for the treatment, protection, care, removal of make-up from and/or cleansing of the skin, the lips and/or the hair, and/or the application of make-up to the skin and/or the lips.

The subject of the present invention is also a method for the cosmetic treatment of the skin, including the scalp, the hair and/or the lips, characterized in that a cosmetic composition as defined above is applied to the skin, the hair and/or the lips.

The following examples illustrate the invention. A.M. means therein "as active material". The quantities are indicated as a percentage by weight unless otherwise stated.

EXAMPLE 1

Gel for Cleansing of or Removing Make-Up from the Face

| | | |
|---|---|---|
| ACUYLN 33 ® from ROHM-HAAS | 5 | % A.M. |
| Sodium lauryl ether sulphate (TEXAPON N702 PATE from HENKEL, at 70% of A.M. in water) | | |
| Glycerin | 6 | % A.M. |
| Preservatives | 3 | % |
| Sodium hydroxide at 10% | qs | |
| Water | qs pH | |
| | qs 100 | % |

Procedure: The water, the glycerin, the surfactant and the preservatives are mixed at room temperature (about 20° to 25° C.). The ACUYLN 33 is added thereto and the mixture is homogenized. The pH is adjusted to 5.85 with sodium hydroxide.

An iridescent gel of pH 5.85 is obtained. This gel has a viscosity at T0, measured using a No. 3 or 4 rotor (Rheomat RM180 at room temperature, that is to say at about 25° C., at 200 s$^{-1}$), of 4.8 poises (0.48 Pa.s).

COMPARATIVE EXAMPLE 1

ACUYLN 33 is replaced, in Example 1, with an equivalent quantity of SYNTHALEN W2000 (3V SA) (5% by weight of A.M.).

A noniridescent colourless transparent gel is obtained.

EXAMPLE 2

Gel for Removing Make-Up from or Cleansing the Face

| | | |
|---|---|---|
| ACUYLN 33 ® from ROHM-HAAS | 5 | % A.M. |
| Sucrose laurate (at 70% of monoester) (SISTERNA L70-C from SISTERNA at 40% of A.M. in water) | 13 | % A.M. |
| Glycerin | 3 | % |
| Preservatives | qs | |
| Sodium hydroxide | qs pH | |
| Water | qs 100 | % |

The procedure is the same as that of Example 1.

An iridescent gel of pH 5.76 is obtained. This gel has a viscosity at T0, measured using a No. 3 or 4 rotor (Rheomat RM180 at room temperature, that is to say at about 25° C., at 200 s$^{-1}$), of 2.5 poises (0.25 Pa.s).

COMPARATIVE EXAMPLE 2

ACUYLN 33 is replaced, in Example 2, with an equivalent quantity of SYNTHALEN W2000 (3V SA) (5% by weight of A.M.).

A noniridescent colourless gel is obtained.

EXAMPLE 3

Gel for Removing Make-Up from or Cleansing the Face

| | | |
|---|---|---|
| SETALUX 6801 AQ64 (AKZO NOBEL) | 15 | % A.M. |
| Sodium lauryl ether sulphate (TEXAPON N702 PATE from HENKEL, at 70% of A.M. in water) | | |
| Glycerin | 6 | % A.M. |
| Preservatives | 3 | % |
| Sodium hydroxide | qs | |
| Water | qs pH | |
| | qs 100 | % |

The procedure is the same as that of Example 1.

An iridescent translucent gel of pH 6.7 is obtained. This gel has a viscosity at T0, measured using a No. 3 or 4 rotor (Rheomat RM180 at room temperature, that is to say at about 25° C., at 200 s$^{-1}$), of 6 poises (0.6 Pa.s), and it has a conductance, measured using the type CD78 conductimeter from TACUSSEL at 25° C. of 6075 $\mu\Omega^{-1}$.

COMPARATIVE EXAMPLE 3

ACULYN 33 is replaced, in Example 3, with an equivalent quantity of an aqueous dispersion of silica, that is the product marketed by the company Ikeda under the name Opalesque 1015, a 15% dispersion in water of silica particles having a size of about 100 nm, that is the product marketed by the company Ikeda under the name Opalesque 1030, a 30% dispersion in water of silica particles having a size of about 100 nm.

In both cases, a noniridescent white liquid is obtained.

EXAMPLE 4

Make-Up-Removing Gel for the Face

| | | |
|---|---|---|
| ACUYLN 33 ® from ROHM-HAAS | 5 | % A.M. |
| Magnesium laureth-8 sulphate (and) magnesium laureth sulphate (and) sodium oleth sulphate (and) magnesium oleth sulphate (EMPICOL BSD 52 ®) from ALBRIGHT & WILSON* (at 52% of A.M. in water) | 0.3 | % A.M. |
| Disodium cocoamphodiacetate (MIRANOL C2M CONG NP ®) from RHODIA CHIMIE (at 38% of A.M. in water) | | |
| Hexylene glycol | 0.5 | % A.M. |
| Glycerin | 5 | % |
| Preservatives | 3 | % |
| Sodium hydroxide | qs | |
| Water | qs pH 6 | |
| | qs 100 | % |

The procedure is the same as that of Example 1.

An iridescent translucent gel of pH 6 is obtained whose colours vary from blue, green, yellow, to orange depending on the orientation. This gel has a viscosity, after 10 minutes, measured with a No. 3 or 4 rotor (Rheomat RM180 at room temperature, that is to say at about 25° C., at 200 s$^{-1}$), of 15 poises (1.5 Pa.s).

EXAMPLE 5

Make-Up-Removing Gel for the Face

| | | |
|---|---|---|
| SETALUX 6801 AQ64 from AKZO NOBEL | 18 | % A.M. |
| Magnesium laureth-8 sulphate (and) magnesium laureth sulphate (and) sodium oleth sulphate (and) magnesium oleth sulphate (EMPICOL BSD 52 ®) from | 0.3 | % A.M. |

-continued

| | | |
|---|---|---|
| ALBRIGHT & WILSON* (at 52% of A.M. in water) | | |
| Disodium cocoamphodiacetate (MIRANOL C2M CONG NP ®) from RHODIA CHIMIE (at 38% of A.M. in water) | 0.5 | % A.M. |
| Hexylene glycol | 5 | % |
| Glycerin | 3 | % |
| Preservatives | qs | |
| Sodium hydroxide | qs pH 7.5 | |
| Water | qs 100 | % |

The procedure is the same as that of Example 1.

An iridescent milky fluid gel of pH 7.5 is obtained whose colours vary from blue to green depending on the orientation. This gel has a viscosity, after 10 minutes, measured with a No. 3 or 4 rotor (Rheomat RM180 at room temperature, that is to say at about 25° C., at 200 s$^{-1}$), of 4 poises (0.4 Pa.s).

EXAMPLE 6

Anti-Inflammatory Gel

| | | |
|---|---|---|
| ACULYN 33 ® from ROHM-HAAS | 5 | % A.M. |
| POE (20) sorbitan monooleate (HLB 15) TWEEN 80 ® from the company UNIQEMA with HLB 15 | 4 | % |
| Ursolic acid from the company CRODAROM | | |
| Glycerin | 0.4 | % |
| Preservatives | 3 | % |
| Sodium hydroxide | qs | |
| Water | qs pH 6 qs 100 | g |

The procedure is the same as that of Example 1.

An iridescent translucent gel of pH 6 is obtained whose colours vary from blue, green, yellow, to orange depending on the orientation. This gel has a viscosity, after 10 minutes, measured with a No. 3 or 4 rotor (Rheomat RM180 at room temperature, that is to say at about 25° C., at 200 s$^{-1}$), of 15 poises (1.5 Pa.s).

What is claimed is:

1. A method for cleansing the skin, said method comprising cleansing the skin of a human with a cosmetic composition comprising at least one water-soluble surfactant and monodisperse particles of polymer in aqueous dispersion, said particles having a mean size of from 50 to 300 nm and the quantity of said particles is at least 3% by weight relative to the total weight of the composition, wherein said surfactant has an HLB equal to or greater than 11.

2. The method according to claim 1, wherein the dispersion and/or the composition exhibits a colorimetric difference ranging from 2 to 100.

3. The method according to claim 1, wherein the turbidity of the composition is greater than 100.

4. The method according to claim 1, wherein the viscosity of the composition is from 0.01 Pa.s to 10 Pa.s.

5. The method according to claim 1, wherein the surfactant is chosen from the group consisting of nomonic surfactants, anionic surfactants, zwitterionic surfactant, amphoteric surfactants and mixtures thereof.

6. The method according to claim 1, wherein the surfactant is chosen from the group consisting of esters of polyols, esters of fatty acids, esters of polyethylene glycols, esters of fatty acids, derivatives of fatty alcohol, derivatives of polyols, oxyalkylenated derivatives of fatty alcohol, oxyalkylenated derivatives of polyols, carboxylates, acyl sarcosinates, alkyl sulphates, alkyl ether sulphates, oxyethylenated derivatives of ether sulphates, sulphonates, taurates, N-acyl-N-methyltaurates, N-acylglutamates, isethionates, N-acylisethionates, N-acylglycinates, sulphosuccinates, alkyl sulphoacetates, phosphates, alkyl phosphates, anionic derivatives of alkyl polyglycoside, polypeptides, soaps, betaines, N-alkylamidobetaines, derivatives of N-alkylamidobetaines, glycine derivatives, sultaines, alkyl polyaminocarboxylates, alkyl amphoacetates, and mixtures thereof.

7. The method according to claim 1, wherein the polymer particles comprise a polymer obtained from one or more monomers chosen from the group consisting of styrene, butadiene, ethylene, acrylonitrile, chloroprene, vinylidene chloride, isoprene, isobutylene, vinyl chloride, acrylic acid, methacrylic acid, vinylacetic acid, maleic acid, crotonic acid, itaconic acid, esters of acrylic acid, esters of methacrylic acid, esters of vinylacetic acid, esters of maleic acid, esters of crotonic acid, esters of itaconic acid, and mixtures thereof.

8. The method according to claim 1, wherein the polymer particles comprise at least one anionic polymer.

9. The method according to claim 1, wherein the polymer particles comprise homopolymers of acrylic acid, copolymers of acrylic acid, styrene derivatives, fluorinated derivatives, silicone-based derivatives, or diisocyanate derivatives.

10. The method according to claim 1, wherein the quantity of polymer particles is from 3 to 50% relative to the total weight of the composition.

11. The method according to claim 1, wherein the quantity of surfactant is from 0.5 to 50% by weight relative to the total weight of the composition.

12. The method according to claim 1, wherein the composition further comprises at least one active agent.

13. The method according to claim 1, further comprising 30 to 96.5% by weight of water relative to the total weight of the composition.

14. The method according to claim 1, further comprising one or more solvents chosen from the group consisting of alcohols comprising 1 to 8 carbon atoms, polyols, sugars and mixtures thereof.

15. The method according to claim 1, wherein the quantity of surfactant is from 2 to 40% by weight relative to the total weight of the composition.

16. The method according to claim 1, wherein the quantity of polymer particles is from 3.5 to 40% by weight relative to the total weight of the composition.

17. An iridescent composition for topical application comprising at least one water-soluble surfactant and monodisperse particles of polymer in aqueous dispersion, said particles having a mean size of from 50 to 300 nm and the quantity of said particles is at least 3% by weight relative to the total weight of the composition, wherein said surfactant has an HLB equal to or greater than 11, wherein the polymer particles are chosen from the group consisting of particles of acrylic acid/ethyl acrylate copolymer, particles of styrene/butyl acrylate/methyl methacrylate/methacrylic acid hybrid copolymer, and mixtures thereof.

* * * * *